US00PP30183P2

(12) United States Plant Patent
Miller

(10) Patent No.: US PP30,183 P2
(45) Date of Patent: Feb. 5, 2019

(54) ***SALVIA* 'SYRACUSE'**

(50) Latin Name: *Salvia microphylla*
Varietal Denomination: Syracuse

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 6 days.

(21) Appl. No.: 15/731,607

(22) Filed: Jul. 8, 2017

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Anne Marie Grunberg
(74) *Attorney, Agent, or Firm* — Cassandra Bright

(57) ABSTRACT

A new and distinct *Salvia* cultivar named 'Syracuse' is disclosed, characterized by an upright, compact plant form, abundance of small rich coral pink flowers. Plants become stoloniferous with maturity and resist breakage. The new variety is a *Salvia microphylla*, normally produced as an outdoor garden or container plant.

2 Drawing Sheets

Figure 1:
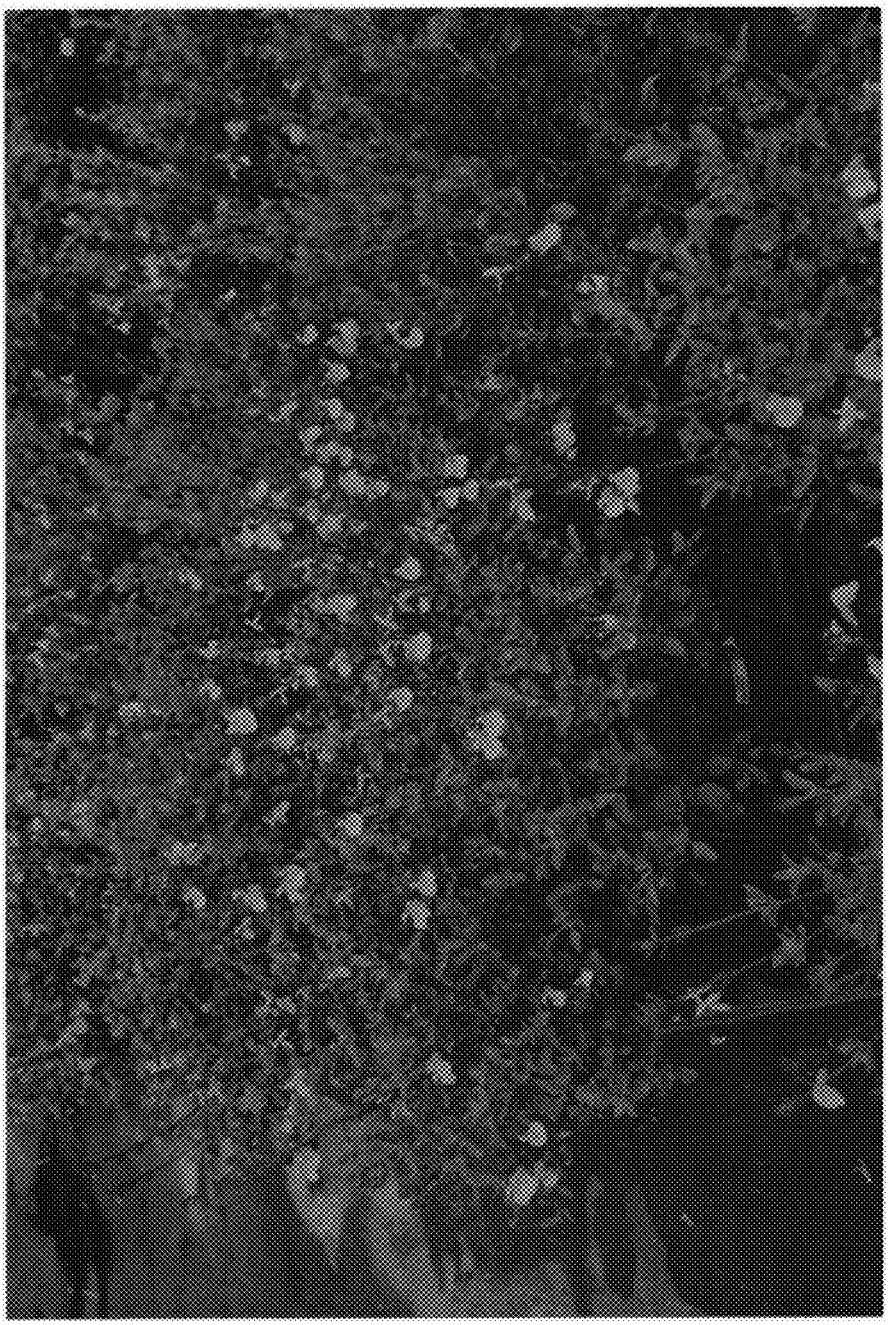

Latin name of the genus and species: *Salvia microphylla*.
Variety denomination: 'Syracuse'.

BACKGROUND OF THE INVENTION

The new *Salvia* cultivar is a product of a planned breeding program conducted by the inventor, Luen Miller, in Royal Oaks, Calif. The objective of the breeding program was to produce new *Salvia* varieties with denser plant habits, strong garden performance, in a range of flower colors. The open pollination resulting in this new variety was made during Summer of 2009.

The seed parent is an unpatented, proprietary, *Salvia microphylla*. The pollen parent is unknown as it was an open pollination breeding program. The new variety was identified as a potentially interesting selection in June 2010, at a commercial nursery in Royal Oaks, Calif.

Asexual reproduction of the new cultivar 'Syracuse' by terminal vegetative cuttings was first performed during June of 2010, at a commercial nursery in Royal Oaks, Calif. Subsequent propagation has shown that the unique features of this cultivar are stable and reproduced true to type on successive generations.

SUMMARY OF THE INVENTION

The cultivar 'Syracuse' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Syracuse' These characteristics in combination distinguish 'Syracuse' as a new and distinct *Salvia* cultivar:

1. Rich coral pink flower color.
2. Vigorous, upright, compact plant form.
3. Excellent branch resilience and resistance to breakage
4. Small flowers, produced heavily over a longer season.

PARENT COMPARISON

Plants of the new cultivar 'Syracuse' are similar to plants of the seed parent in most horticultural characteristics, however, plants of the new cultivar 'Syracuse' differ in the following:

1. The new variety has a much lighter flower color. The parent variety has dark pink flowers.
2. Flowers of the new variety are approximately half the size of flowers of the seed parent.
3. Plants of the new variety are more compact and dense in habit.
4. Plants of the new variety have stronger, semi-stoloniferous roots not seen in the parent variety.

COMMERCIAL COMPARISON

Plants of the new cultivar 'Syracuse' can also be compared to the commercial variety *Salvia* 'EGGBEN002', U.S. Plant Pat. No. 24,153. These varieties are similar in most horticultural characteristics; however 'Syracuse' differs in the following:

1. Flowers of the new variety are approximately half the size of flowers of this comparator.
2. Inflorescences of the new variety are taller and narrower than those of this comparator.
3. The new variety produces more leaves per branch than this comparator.
4. Flower color of the new variety is a different shade, and does not have the white lip found in this comparator.

Plants of the new cultivar 'Syracuse' can also be compared to the commercial variety *Salvia* 'BALMIRPINK', patent status unknown. These varieties are similar in most horticultural characteristics; however 'Syracuse' differs in the following:

1. Flowers of the new variety have a narrower lower lip.
2. Branches are significantly more flexible and breakage resistant than those of this comparator.

3. Roots are significantly more stoloniferous than those of this comparator.

BRIEF DESCRIPTION OF THE PHOTOGRAPHS

The accompanying photograph in FIG. 1 illustrates in full color typical plants of 'Syracuse' grown in a nursery, in Royal Oaks, Calif., in commercial 1 quarter containers. FIG. 1 includes other *Salvia* varieties with darker pink and lavender flowers. Plants of 'Syracuse' are the coral pink flowered plants in the center and lower portion of the photograph.

Figure 2:
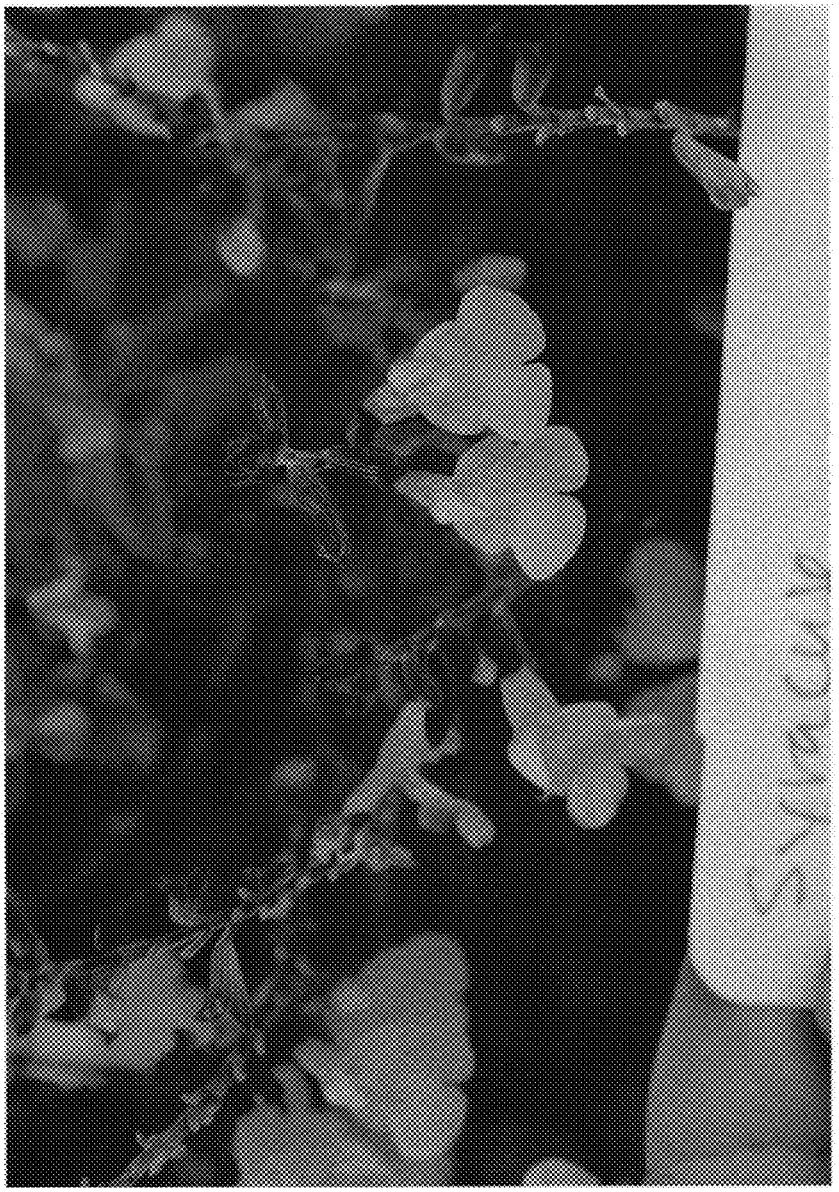

FIG. 2 illustrates in full color typical flowers of 'Syracuse'. Age of the plants photographed are approximately 26 weeks from unrooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Syracuse' plants grown in a nursery in Royal Oaks, Calif. The growing temperature ranged from approximately 10° C. to 30° C. The nursery is un-shaded, giving bright, normal sunlight conditions. Measurements and numerical values represent averages of typical plant types.

Botanical classification: *Salvia microphylla* 'Syracuse'.

PROPAGATION

Root description: Fine, densely fibrous, becoming moderately stoloniferous with maturity. Colors include Green-White 157D on new growth and Orange-White 159C, Grey-Brown 199B and 199C for older roots and stolons.

PLANT

Growth habit: Upright and somewhat outwardly angled.

Pot size of plant described: 5 gallon pot.

Height: Approximately 40 cm to top of foliage. Approximately 55 cm to top of flowering plane. Measured from soil level of pot.

Plant spread: Approximately 75 cm.

Growth rate: Rapid.

Branching characteristics: Very well branched; Approximately 4 to 5 branches emerging from a pinch, which branch into another 4 to 5 primary lateral branches.

Length of primary lateral branches: Approximately 18 to 30 cm.

Diameter of lateral branches: Approximately 0.3 cm.

Quantity of lateral branches: About 12 to 28.

Stem:

- *Color*.—One side typically near RHS Yellow-Green 144B, the opposite side near Greyed-Purple N186C. Older growth near Greyed-Purple 187A. Oldest growth woody.
- *Texture*.—Very slightly pubescent and typically 4 ribs. Older growth scaly.

Internode length: Average range 3.5 to 4.0 cm.

Age of plant described: Approximately 1.5 years.

FOLIAGE

Leaf:

- *Arrangement*.—Opposite.
- *Quantity*.—Average range 18 to 36 fully expanded and immature leaves per main branch with side branches.
- *Average length*.—Approximately 2.1 cm. including petiole.
- *Average width*.—Approximately 1.0 cm.
- *Shape of blade*.—Obovate.
- *Apex*.—Acute.
- *Base*.—Broad attenuate.
- *Attachment*.—Stalked.
- *Margin*.—Crenate.
- *Texture of top surface*.—Matte, glabrous. Finely reticulated.
- *Texture of bottom surface*.—Matte, glabrous. Prominent reticulated veins.
- *Color*.—Young foliage upper side: Near RHS Green 137A. Young foliage under side: Near RHS Green 138A. Mature foliage upper side: Near RHS Green 137A. Mature foliage under side: Near RHS Green 138A.
- *Venation*.—Type: Reticulate. Venation color upper side: Near RHS Yellow-Green 145A. Venation color under side: Near RHS Yellow-Green 144B.
- *Petiole*.—Average Length: Approximately 0.3 cm. Diameter: Approximately 0.1 cm. Color: Near Yellow-Green 144B.

Other: Foliage slightly aromatic.

FLOWER

Natural flowering season: Flowering from early Spring through late Summer.

Inflorescence type and habit: Flowers arranged in verticillasters on spikes.

Flower longevity on plant: Individual flowers last approximately 7 to 10 days on the plant. Each spike lasts approximately 6 to 8 weeks with flowers. Corolla self-cleaning, calyx persistent.

Quantity of flowers: About 10 to 16 buds and 12 to 20 fully opened flowers per spike, at one time. Mature plants have approximately 40 to 60 spikes.

Spike size:

- *Diameter*.—Approximately 4.5 cm.
- *Height*.—Approximately 10.0 to 17.0 cm.

Individual flowers:

Size:

- *Diameter*.—Approximately 1.1 cm.
- *Length*.—Approximately 2.6 cm.

Fragrance: Moderately strong musty aromatic scent.

Corolla:

- *Petal arrangement*.—The corolla is sympetalous and typically bilabiate with 2 small, fully fused lobes forming a single upper lip and 3 larger fused lobes forming a lower lip.
- *Margin*.—Entire.
- *Tip shape*.—Upper lip tip obtuse, lower lip tip retuse.
- *Length*.—Upper lip Approximately 0.8 cm. Lower lip Approximately 0.9 cm. Tube length Approximately 1.5 cm.

*Width*.—Upper lip: Approximately 0.4 cm, lower lip Approximately 1.2 cm. Tube width: Approximately 0.5 cm.

*Texture*.—Upper lip: Glabrous interior, very slightly pubescent exterior. Lower lip: Glabrous all surfaces.

Color:

*Upper lip*.—When opening: Inner surface: Near RHS Red 49D. Outer surface: Near RHS Red-Purple N57C. Fully opened: Inner surface: Near RHS Red 49D. Outer surface: Near RHS Red-Purple 61C. Fading: Inner surface: Near RHS Red 49D. Outer surface: Near RHS Red-Purple 61D.

Color:

*Lower lip*.—When opening: Inner surface: Near RHS Red 52A. Outer surface: Near RHS Red 52B. Fully opened: Inner surface: Near RHS Red 52B. Outer surface: Near RHS Red 54B. Fading: Inner surface: Near RHS Red 55A. Outer surface: Near RHS Red 55B.

Color:

*Tube*.—When opening: Inner surface: Near RHS Red-Purple 69B. Outer surface: Near RHS Red-Purple 61D. Fully opened: Inner surface: Near RHS Red 55C. Outer surface: Near RHS Red-Purple N57C. Fading: Inner surface: Near RHS Red 55C. Outer surface: Near RHS Red-Purple N57D.

Bud: Flower bud includes immature calyx which completely surrounds immature corolla.

*Shape*.—Ovoid.

*Length*.—Approximately 1.2 cm.

*Diameter*.—Approximately 0.4 cm.

*Color*.—Near RHS Red-Purple N57B.

Calyx:

*Length*.—Approximately 1.0 cm.

*Diameter*.—Approximately 0.7 cm.

*Shape*.—Tubular.

Sepals:

*Shape*.—Quantity per flower: 3, fused to form a tube. Unfused apex.

*Length*.—Approximately 0.3 cm unfused portion.

*Width*.—Approximately 0.4 cm.

*Margin*.—Entire.

*Apex*.—Short apiculate.

*Texture*.—Softly pubescent and ridged.

*Color*.—Immature: Base near Green 138A, center Greyed-Purple N187B, apex N186A. Stripes over entire surface near N187A. Mature: Base near Green 138A, apex N186A. Stripes over entire surface near N187A.

Peduncle:

*Length*.—Average 3.5 cm.

*Diameter*.—0.3 cm.

*Color*.—One side typically near RHS Yellow-Green 144B, the opposite side near Greyed-Purple N187A.

*Orientation*.—Straight. Occurring at approximately 15 degree angle from center of plant.

*Strength*.—Moderately strong.

*Texture*.—Glabrous at maturity, very slightly pubescent when immature. Ridged.

Pedicels:

*Length*.—Average range 0.2 to 0.3 cm.

*Diameter*.—0.1 cm.

*Color*.—Near RHS Greyed-Purple N187A.

*Orientation*.—Straight, approximately 25 degree angle from attachment.

*Strength*.—Strong.

*Texture*.—Pubescent.

REPRODUCTIVE ORGANS

Stamens:

*Number*.—2.

*Filament length*.—Approximately 0.6 cm.

*Filament color*.—Near RHS White N155B, very slightly flushed Red 55C.

Anthers:

*Shape*.—Linear.

*Length*.—0.1 cm.

*Color*.—Near RHS Yellow-Orange 22A.

*Pollen*.—Scant pollen observed, colored near RHS Yellow 12C.

Pistil:

*Number*.—1.

*Length*.—Approximately 2.4 cm.

*Style*.—Length: Approximately 2.0 cm. Color: Near RHS White N155D.

*Stigma*.—Shape: Forked. Color: Near RHS Red-Purple 60D. Ovary: Colored near RHS Green 138D, oblong, approximately 0.2 cm long and 0.1 in diameter.

OTHER CHARACTERISTICS

Seeds and fruits: Seed production not observed. Reduced and malformed ovary, plant may be sterile.

Disease/pest resistance: Neither resistance nor susceptibility to pathogens and pests common to *Salvia microphylla* have been observed.

Temperature tolerance: The new variety tolerates temperatures within USDA zones 3 to 8.

What is claimed is:

1. A new and distinct cultivar of *Salvia* plant named 'SYRACUSE' as herein illustrated and described.

* * * * *